United States Patent
Bankert et al.

(10) Patent No.: US 11,497,836 B2
(45) Date of Patent: *Nov. 15, 2022

(54) SYSTEMS AND METHODS FOR FORMING MATERIALS IN SITU WITHIN A MEDICAL DEVICE

(71) Applicant: Endologix LLC, Irvine, CA (US)

(72) Inventors: Charles Bankert, Oceanside, CA (US); Paolo Mendoza, Huntington Beach, CA (US); Stefan Schreck, San Clemente, CA (US)

(73) Assignee: Endologix LLC, Irvine, CA (US)

( * ) Notice: Subject to any disclaimer, the term of this patent is extended or adjusted under 35 U.S.C. 154(b) by 13 days.

This patent is subject to a terminal disclaimer.

(21) Appl. No.: 16/272,809

(22) Filed: Feb. 11, 2019

(65) Prior Publication Data

US 2019/0167856 A1 Jun. 6, 2019

Related U.S. Application Data

(63) Continuation of application No. 14/776,385, filed as application No. PCT/US2014/021928 on Mar. 7, 2014, now Pat. No. 10,201,638.

(Continued)

(51) Int. Cl.
*A61B 17/12* (2006.01)
*A61L 31/14* (2006.01)
(Continued)

(52) U.S. Cl.
CPC ...... *A61L 31/048* (2013.01); *A61B 17/12113* (2013.01); *A61B 17/12136* (2013.01);
(Continued)

(58) Field of Classification Search
CPC ...... A61F 2/01; A61F 2/013; A61B 17/12113; A61B 17/12118; A61B 17/12136;
(Continued)

(56) References Cited

U.S. PATENT DOCUMENTS 7,238,364 B2    7/2007  Sawhney et al.
7,872,068 B2 *  1/2011  Khosravi .............. A61L 24/046
                                                    524/560

(Continued)

FOREIGN PATENT DOCUMENTS

CN        101489622 A      7/2009
WO    WO-2007/142916 A2   12/2007
WO    WO-2011111040 A2 *   9/2011  ............... A61B 1/31

OTHER PUBLICATIONS

European Office Action dated Apr. 23, 2019, from application No. 14712991.0.

(Continued)

*Primary Examiner* — Kathleen S Holwerda
(74) *Attorney, Agent, or Firm* — Foley & Lardner LLP

(57) ABSTRACT

A method for forming a material in an in situ medical device by initiating polymerization of water soluble polymer precursors in an aqueous solution during or after transport of the polymerizable solution from its storage container to a space inside the in situ medical device is described. The stored aqueous solution with water soluble precursors lacks a free radical initiator which, in a powder form, is introduced into the aqueous solution during or after its transport into the space inside the in situ medical device. This storage and delivery system provides greater stability to the stored aqueous solution, allowing it to be stored at ambient temperature and providing extended shelf life over the solutions used in existing in situ polymerization systems. The flexibility to store and deliver/transport only one aqueous solution, instead of requiring the use of two different solutions, is also a benefit.

21 Claims, 8 Drawing Sheets

Related U.S. Application Data

(60) Provisional application No. 61/785,445, filed on Mar. 14, 2013.

(51) Int. Cl.
*A61L 31/04* (2006.01)
*A61L 31/06* (2006.01)

(52) U.S. Cl.
CPC ............ *A61L 31/041* (2013.01); *A61L 31/06* (2013.01); *A61L 31/14* (2013.01); *A61L 31/143* (2013.01); *A61L 2400/06* (2013.01)

(58) Field of Classification Search
CPC ........ A61B 17/12031; A61B 17/12036; A61B 17/1204; A61B 17/12027; A61B 2017/1205; A61L 31/06; A61L 31/041; A61L 31/048; A61L 31/14; A61L 31/143; A61L 2400/06
See application file for complete search history.

(56) References Cited

U.S. PATENT DOCUMENTS

| | | | | |
|---|---|---|---|---|
| 8,197,527 B2* | 6/2012 | Borillo | ............. | A61B 17/12136 623/1.11 |
| 9,289,536 B2* | 3/2016 | Bankert | ................ | A61L 31/143 |
| 10,201,638 B2* | 2/2019 | Bankert | .................... | A61P 9/10 |
| 2003/0134032 A1* | 7/2003 | Chaouk | .................. | A61L 24/06 427/2.24 |
| 2005/0010285 A1* | 1/2005 | Lambrecht | ............ | A61F 2/2427 623/2.18 |
| 2005/0107738 A1* | 5/2005 | Slater | ................... | A61M 25/10 604/96.01 |
| 2013/0023920 A1* | 1/2013 | Terliuc | .................... | A61B 1/32 606/192 |
| 2013/0281979 A1* | 10/2013 | Arnim | ............... | A61M 25/0136 604/509 |

OTHER PUBLICATIONS

Chinese Office Action dated Aug. 21, 2018, from application No. 201480015060.9.
Chinese Office Action dated Dec. 29, 2017, from application No. 201480015060.9.
Chinese Office Action dated Feb. 4, 2017, from application No. 201480015060.9.
European Office Action dated Jun. 25, 2018, from application No. 14712991.0.
European Office Action dated Oct. 17, 2017, from application No. 14712991.0.
International Search Report and Written Opinion dated May 20, 2014, from application No. PCT/US2014/021928.
Japanese Office Action dated Apr. 3, 2018, from application No. 2016-500882.
Japanese Office Action dated Jul. 31, 2018, from application No. 2016-500882.
U.S. Final Office Action dated May 16, 2018, from U.S. Appl. No. 14/776,385.
U.S. Non-final Office Action dated Jan. 23, 2018, from U.S. Appl. No. 14/776,385.
U.S. Non-final Office Action dated Mar. 27, 2015, from U.S. Appl. No. 14/201,332.
U.S. Notice of Allowance dated Dec. 8, 2015, from U.S. Appl. No. 14/201,332.
U.S. Notice of Allowance dated Sep. 27, 2018, from U.S. Appl. No. 14/776,385.
Japanese Office Action dated May 7, 2020, from application No. 2019-098453.
Japanese Office Action dated Mar. 9, 2021, from application No. 2019-098453.

* cited by examiner

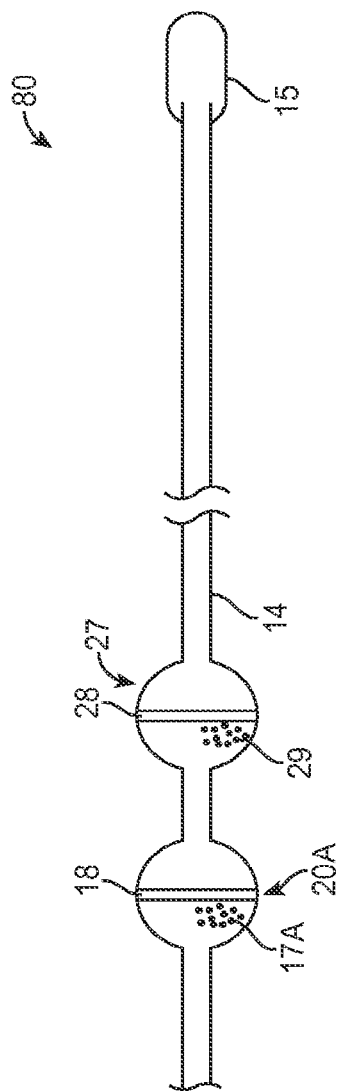

SYSTEMS AND METHODS FOR FORMING MATERIALS IN SITU WITHIN A MEDICAL DEVICE

This application is a continuation of U.S. patent application Ser. No. 14/776,385, filed Sep. 14, 2015, which is a National Stage Entry of PCT/US2014/021928, filed Mar. 7, 2014, which claims priority to U.S. Provisional Patent Application No. 61/785,445 filed on Mar. 14, 2013 and entitled "Method for Forming Materials In Situ Within a Medical Device," the full disclosures of each of which are incorporated herein by reference.

BACKGROUND

Abdominal Abdominal Aortic Aneurysms (AAA) are weakened areas in the aorta that form balloon-like bulges, or sacs, in approximately the abdominal area. As blood flows through the aorta, the pressure of the blood pushes against the weakened wall, causing it to enlarge and often rupture. Ruptured AAA is a major cause of death in the United States.

In the past, clips and open surgery were the traditional interventional treatments for AAA. More recently, endografts, sometimes with stents for added stability, have been placed across the aneurysm to reduce the pressure on the aneurysm wall and prevent its enlargement and rupture.

Most recently, there have been described systems wherein an expandable member of a device is introduced into the aneurysmal sac by means of minimally invasive surgical (MIS) techniques, e.g., guidance through the vasculature of a human patient using a guidewire introduced into the patient for that purpose. Flowable precursor materials are introduced into the expandable member, the precursor materials undergo chemical reaction and cause the expandable member to expand and conform to the shape of the aneurysmal sac. As the materials harden, they lock the expandable member in place in the patient and stabilize the aneurysm. See for example, U.S. Pat. Pub. Nos. 7,872,068; 8,044,137; and U.S. 2006/0222596, the contents of which are hereby incorporated by reference herein in their entirety. The expandable member may be, for example, a single-walled or double-walled balloon or an inflatable cuff. Other examples of devices having an inflatable or expandable member are provided, for example, in PCT Application Pub. No. WO 00/51522, U.S. Pat. Pub. Nos. 5,334,024; 5,330, 528, 6,1312,462; 6,964,667; 7,001,431; 2004/0204755; and 2006/0025853A1, the contents of which are hereby incorporated by reference herein in their entirety. The flowable precursor materials are typically polymer precursors which polymerize and cross-link to form hydrogels. One preferred type of polymer precursor is a material that can be polymerized by free radical polymerization. Typically this involves the polymerization/cross-linking of two prepolymers, each having terminal reactive groups that are susceptible to free radical polymerization, such as acrylates and methacrylates.

The polymerization is effected by combining both prepolymers with a thermally activated low temperature free radical initiator and an initiator catalyst at physiological temperature.

In order to avoid premature polymerization, i.e., prior to mixing all the components and allowing them to polymerize in situ in the expandable device, the components are typically stored in two separate aqueous solutions, one solution comprising one polymer precursor and the free radical initiator, and the other solution comprising the other polymer precursor and the initiator catalyst. In this way, the two polymer precursors are kept apart, as are the free radical initiator and the initiator catalyst.

In practice, the two solutions are concomitantly delivered and then mixed, either ex vivo in a manifold, or in the expandable device itself.

Because of the instability of thermally activated low temperature free radical initiators, the solutions containing the components must necessarily be kept frozen, i.e., at zero degrees Celsius or lower, until needed. Even so, the useful shelf life of the device or kit comprising such solutions is only 12 to 18 months.

The necessity that the solutions be kept frozen is a serious practical disadvantage, inasmuch as the solutions cannot easily be thawed and be ready for use as soon as a patient presents with an AAA that needs immediate treatment, particularly since rapid thawing by conventional techniques using large temperature differentials, e.g., hot water or microwave defrosting, cannot be used because of the thermal activation of the initiator.

It would be desirable to have materials and methods for using such materials, such that storage of the aqueous solutions used for treatment could be at or near ambient temperature, allowing for immediate use when required, and having a useful shelf life of at least 2 years.

It would further be desirable to be able to administer only one solution, rather than two, thus avoiding the necessity for mixing in a manifold or other device, and ensuring homogeneity of the material being polymerized.

SUMMARY OF THE INVENTION

What is needed is an improved method for stabilizing AAA-treating devices. These methods are described herein, including materials and methods of stabilizing implanted medical devices by introducing flowable precursor materials that expand an expandable member of the device to set the device in place, with the precursors then hardening to keep the device in place. Previous devices and methods have been described in detail in, e.g., U.S. Pat. No. 8,044,137, cited above, the contents of which are hereby incorporated by reference herein in their entirety.

Embodiments described herein provide methods that allow for simpler and more practical stabilization of implanted medical devices, in particular, elimination of the need to keep the materials frozen until use, increased shelf life, and the ability to use only one solution to initiate the process.

In particular, one embodiment is directed to a method of forming a material in situ by increasing the volume of an expandable member of a medical device in a patient by:
 a. introducing into a tube in communication with a space inside the expandable member, or directly into the expandable member, a flowable aqueous solution comprising a first and a second water soluble polymer precursor, each water soluble polymer precursor having terminal functional groups, and, optionally, an initiator catalyst,
 b. introducing into the flowable aqueous solution from step (a) a thermally activated low temperature free radical initiator in powder form,
 c. allowing the free radical initiator to dissolve in the flowable aqueous solution,
 d. if not previously introduced in step (a), introducing the initiator catalyst into the solution from step (c), and
 e. allowing functional groups on the polymer precursors to undergo covalent bonding to form a solid and substantially non-biodegradable material in the space inside the expandable member.

The flowable aqueous solution may be formed by the mixture of a first and a second source solution, each introduced into a separate filling tube, each source solution comprising one of the polymer precursors, or if only one source solution comprising both the first and second polymer precursors is employed, the flowable aqueous solution is identical to the one source solution and is introduced into a single filling tube. The catalyst may be present in a source solution, or added before or after the initiator is introduced.

This method allows for the free radical initiator to be absent from the source solutions being introduced and, instead, to be kept in powder form and introduced into the flowable aqueous solution only at the time the polymerization is desired. This material in powder form may be present in a filter upstream from the expandable member, in the expandable member itself, or in a container in communication with the expandable member. As a result of the free radical initiator not being present in the source solution(s), it is now possible and desirable to combine both polymer precursors into one source solution, and thereby administer a single source solution to initiate the polymerization process.

BRIEF DESCRIPTION OF THE DRAWINGS

FIG. 8 depicts a schematic cross-section of a portion of another embodiment of an apparatus used to practice the method described herein.

The drawings are intended to depict various components and their relationship to each other. The components are not drawn to scale.

DETAILED DESCRIPTION

As discussed above, previous methods for treating AAA have included forming a material in situ by increasing the volume of an expandable member of a medical device. The expandable member when expanded by flowable material conforms to the shape of the aneurysm in which it is contained, and once allowed to harden, fixes the medical device in place. The material is formed by the free radical polymerization of two polymer precursors in an aqueous solution in the presence of a thermally activated free radical initiator and an initiator catalyst. The polymerization is carried out, for example, inside an endograft comprising a single-walled or double-walled balloon.

Figure 1:
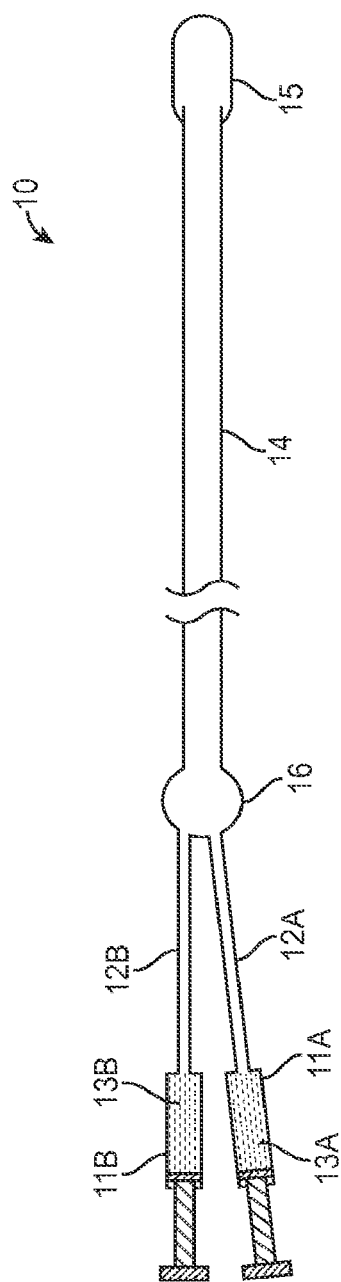
FIG. 1 depicts a schematic cross-section of a prior art apparatus.

FIG. 1 depicts an embodiment of a typical prior art apparatus 10 used to practice previous methods. Two solutions 13A, 13B are in containers 11A, 11B, for example, syringes, that communicate with filling tubes 12A, 12B. In this configuration, one solution comprises a first polymer precursor and either the initiator or the catalyst, and the other solution comprises a second polymer precursor and the other of the initiator and the catalyst. The solutions 13A, 13B are delivered under pressure to a manifold 16 where they are mixed. The manifold may comprise various structures to ensure thorough mixing. The resulting solution is then delivered via tube 14 to the expandable member 15 where polymerization occurs, the expandable member expands to conform to the shape of a surrounding aneurysm (not shown), and time passes to allow the polymerization to progress. Once solution delivery is concluded (the termination of solution injection can be based on pressure sensors attached to the pressurized tubing, e.g., tube 14, or on the basis of achieving delivery of a premeasured or calculated volume needed to fill the aneurysmal space which is desired to be occupied), the tube 14 is withdrawn from the expandable member allowing the polymerizing mixture to be sealed within the expandable member 15. The medical device comprising the expandable member is typically delivered to the site of the aneurysm in the patient by means of a catheter that is put into place over a guidewire. In another embodiment there is no manifold and the two solutions are mixed in the expandable member.

The presence of the initiator in one of the solutions being introduced is problematic in that it necessitates that the solutions and, therefore, the entire apparatus, be kept frozen, and thawed only immediately before delivering into a catheter for treating a patient. Thawing by traditional means involving large temperature differentials such as hot water or microwave treatment is not possible due to the thermal activation of the initiator. At ambient temperature the initiator in the solution is unstable and can result in degradation of the polymer precursor, such as and including premature polymerization, resulting in an unacceptable shelf life.

It has now been found that, surprisingly, by eliminating the initiator from the solution, and introducing it in powder form later in the process, (i) one can avoid having to store the apparatus containing the solutions at freezer temperature, (ii) overall shelf life can be improved, (iii) both polymer precursors can be combined into one solution for delivery, greatly simplifying the procedure, and (iv) the resulting hydrogel is of a quality substantially the same as that prepared by previous methodologies.

Thus, in its broadest aspect, a method described includes a method of forming a material in situ by increasing the volume of an expandable member of a medical device in a patient by:

a. introducing into a tube in communication with a space inside the expandable member, or directly into the expandable member, a flowable aqueous solution comprising a first and a second water soluble polymer precursor, each water soluble polymer precursor having terminal functional groups, and, optionally, an initiator catalyst, b. introducing into the flowable aqueous solution from step (a) a thermally activated low temperature free radical initiator in powder form, c. allowing the free radical initiator to dissolve in the flowable aqueous solution, d. if not previously introduced in step (a), introducing the initiator catalyst into the solution from step (c), and e. allowing functional groups on the polymer precursors to undergo covalent bonding to form a solid and substantially non-biodegradable material in the space inside the expandable member.

Particularly preferred polymer precursors are those that, upon polymerization and cross-linking, will result in a hydrogel having certain desired properties, most notably being a solid and nonbiodegradable material having a swellability of less than about 20% v/v and having a Young's modulus of at least about 100 kiloPascals. To minimize the time required for the MIS (minimally invasive surgical) procedure, but allow sufficient time for the removal of filling tubes from the expandable member, it is preferred that the time for forming the finished hydrogel be from about 30 seconds to about 30 minutes from initiating the polymerization reaction. The polymerization reaction is initiated by the mixture of both polymer precursors, the initiator and the catalyst in solution.

It is preferred that the polymer precursors be water soluble, be soluble with each other, have similar polymerization reactivity to ensure the hydrogel is a random copolymer, and have terminal functional groups. Polymer precursors comprising polyethyleneoxide units, i.e., polyethylene glycols (PEGS), with terminal acrylate or methacrylate functional groups, are particularly preferred. It is also preferred that there be a first polymer precursor that is linear and a second polymer precursor that is branched. The linear polymer precursor provides a long-chain, durable and flexible base for the hydrogel, and the branched polymer precursor provides a high degree of cross-linking for the hydrogel with a network structure having the desired swellability and hardness. A particularly preferred linear polymer precursor is polyethylene glycol terminally derivatized with two acrylate groups and having a molecular weight between about 20 and 50 kiloDaltons, most preferably about 35 kiloDaltons. A particularly preferred branched polymer precursor is an oligomeric branched polyethylene glycol terminally derivatized with three acrylate groups and having a molecular weight of between about 800 Daltons and 1.2 kiloDaltons, most preferably about 1 kiloDalton. The molar ratio of branched polymer precursor to linear polymer is preferably between about 200:1 and about 1000:1, most preferably about 400:1.

Thermally activated low temperature free radical initiators will initiate free radical crosslinking reactions at or near physiological body temperatures. Particularly preferred initiators are sodium persulfate, potassium persulfate and ammonium persulfate. Ammonium persulfate is particularly preferred because of its high water solubility, thereby assuring its complete solubility during the processes described.

Initiator catalysts are used to initiate the polymerization reaction by reaction with the initiator. Preferred catalysts include triethanolamine and tetramethylethylenediamine. Triethanolamine is particularly preferred. It is generally preferred that the initiator and catalyst be present in about equimolar amounts and that the molar ratio of branched polymer precursor to initiator be from about 2:1 to about 15:1, preferably about 7:1.

The aforementioned components (both polymer precursors and, optionally, catalyst) are dissolved in one or two source solutions, preferably in buffered aqueous solutions such as phosphate buffered solutions having a pH desirable for stability of the ester linkages, preferably neutral to slightly acidic, pH 4-7, and providing a hydrogel having a neutral osmolarity with respect to physiological conditions. The initiator as a powder is dissolved later. Sufficient buffered source solution is used to reduce viscosity and ensure that the source solution(s) is flowable. If two source solutions are employed, the first source solution comprises the first polymer precursor and the second source solution comprises the second polymer precursor. The catalyst may be present in one of the source solutions or it may be added later, either before or after introduction of the initiator. Preferably, the catalyst is present in one of the source solutions. In addition, one of the source solutions typically also comprises a radio-opaque agent such as sodium diatrizoate for fluoroscopic visualization. For ease of delivery it is preferable that about equal volumes of the two source solutions be employed. If only one source solution is employed, both polymer precursors, optionally the catalyst, and a radio-opaque agent are present. Preferably the catalyst is present in the source solution.

Figure 2A:
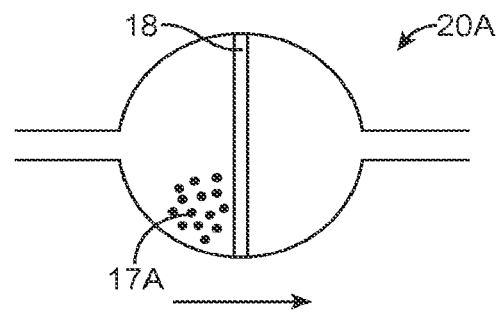
FIG. 2A depicts a schematic cross-section of an embodiment of a filter unit.

In one embodiment depicted in FIG. 2A a filter unit 20A comprises a filter 18. The initiator 17A in powder form is disposed on the upstream side of the filter. The filter unit is disposed in the tube 14 upstream from the expandable member. As the flowable aqueous solution passes through the filter unit, the initiator dissolves therein.

Figure 2B:
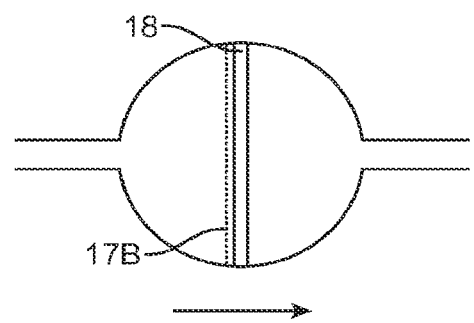
FIG. 2B depicts a schematic cross-section of another embodiment of a filter unit.

In another embodiment the initiator in powder form 17B is immobilized on the upstream side of the filter 18. This is depicted in FIG. 2B. The immobilization may be effected, for example, by capturing the initiator in a sponge or scaffold, by trapping it in small pores or in an erodible solid.

Figure 2C:
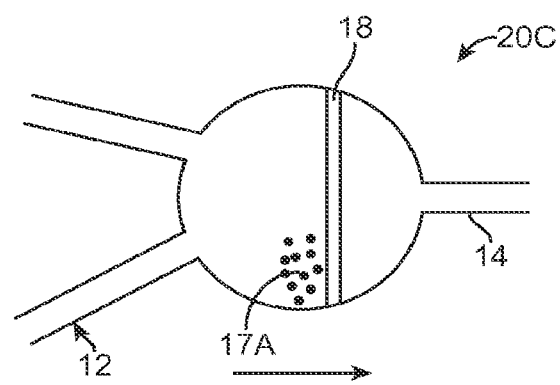
FIG. 2C depicts a schematic cross-section of an embodiment of an integrated manifold/filter unit.

In yet another embodiment depicted in FIG. 2C, two source solutions are utilized and the manifold and filter are shown as integrated into a single unit 20C.

In the aforementioned embodiments in FIGS. 2A-C the filter may be constructed of PTFE, PVDF, polysulfone, polypropylene and other compatible materials with pores sufficiently small to prevent the passage of initiator powder therethrough, but able to allow the passage of solution under pressure without impediment. The arrows depict the direction of flow. A variety of commercially available filter units with the above properties may be used, for example, a 33 mm Millex GP 0.22 µm filter.

Figure 3:
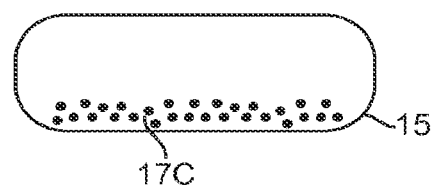
FIG. 3 depicts a schematic cross-section of an embodiment of an expandable member.

In another embodiment depicted in FIG. 3 the initiator in powder form 17C is disposed in the expandable member 15. This material then dissolves in the flowable aqueous solution as it flows into the expandable member.

Figure 4:
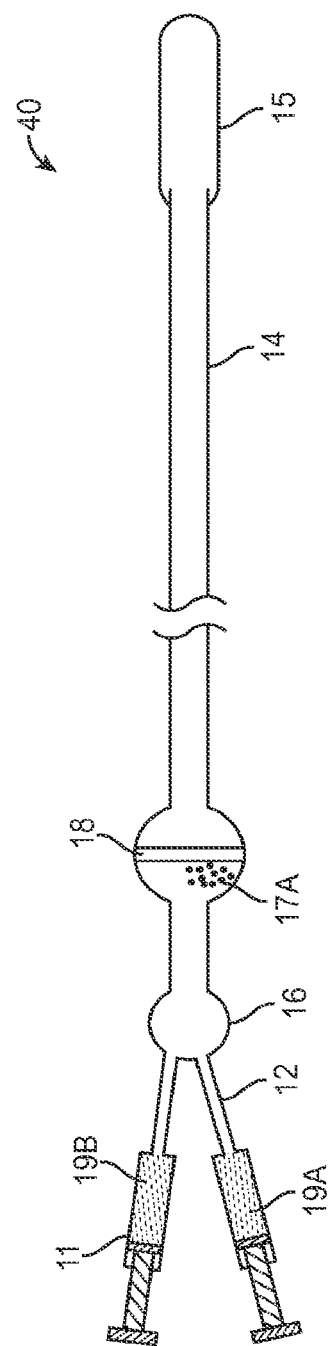
FIG. 4 depicts a schematic cross-section of an embodiment of an apparatus used to practice the method described herein.

One embodiment of an apparatus 40 used to practice the method described is depicted in FIG. 4. The two source solutions 19A, 19B, each comprising one polymer precursor, with one source solution comprising the catalyst, are delivered to manifold 16 and the resulting flowable aqueous solution then is delivered to filter 18 having initiator 17A (or 17B) in powder form disposed on the upstream side thereof and, after the powder dissolves, the resulting solution passes through the filter and is delivered to expandable member 15.

Figure 5:
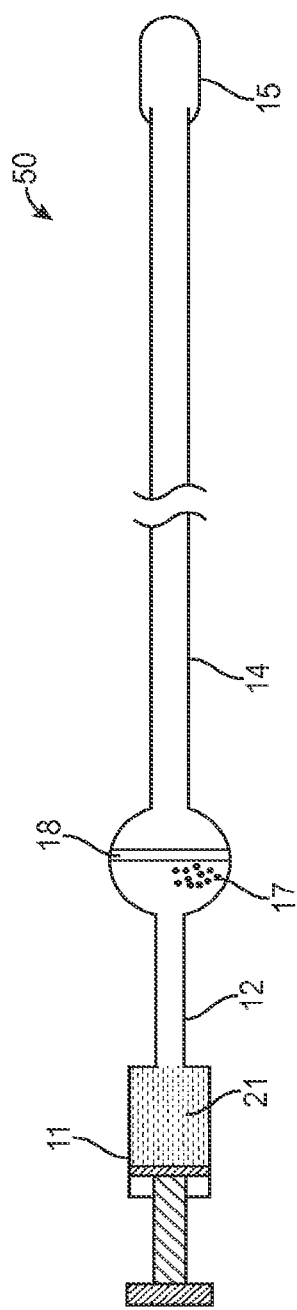
FIG. 5 depicts a schematic cross-section of another embodiment of an apparatus used to practice the method described herein.

Another embodiment of an apparatus 50 used to practice the method described is depicted in FIG. 5. In this embodiment only one source solution 21 is utilized. This solution comprises both polymer precursors and the catalyst, and is delivered to the filter 18 having initiator 17A (or 17B) in powder form disposed on the upstream side thereof and, after the powder dissolves, the resulting solution passes through the filter and is delivered to expandable member 15.

Figure 6:
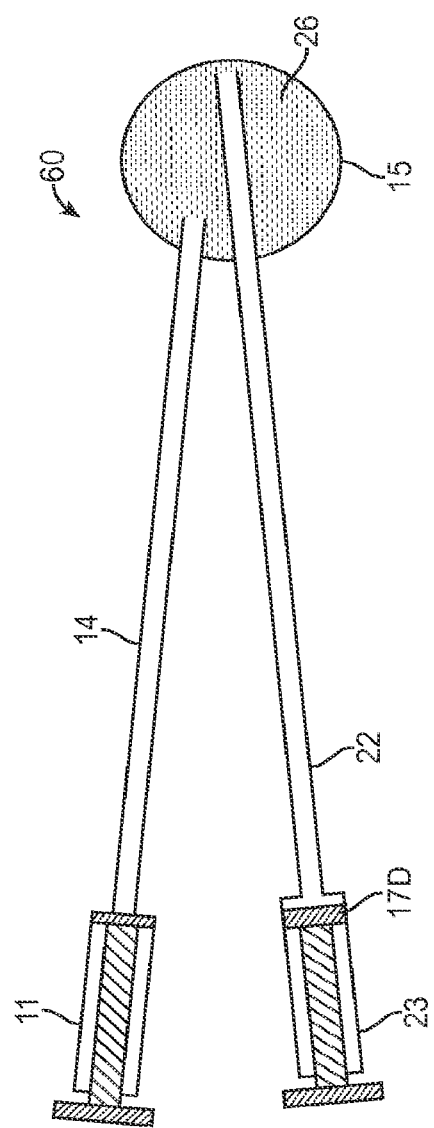
FIG. 6 depicts a schematic cross-section of another embodiment of an apparatus used to practice the method described herein.

Another embodiment of an apparatus 60 used to practice the method described is depicted in FIG. 6. A single source solution is delivered directly to the expandable member 15, depicted as partially expanded. A small portion, for example, 5-10% of the volume of delivered solution 26 is withdrawn via tube 22 into a container 23, for example, a syringe, containing initiator 17D in powder form. After the powder dissolves in delivered solution 26 the resulting solution is returned to the expandable member via tube 22, mixed with delivered solution 26 in the expandable member, and the polymerization reaction is allowed to proceed. In a variation on this embodiment, two source solutions are initially delivered to the expandable member.

Figure 7:
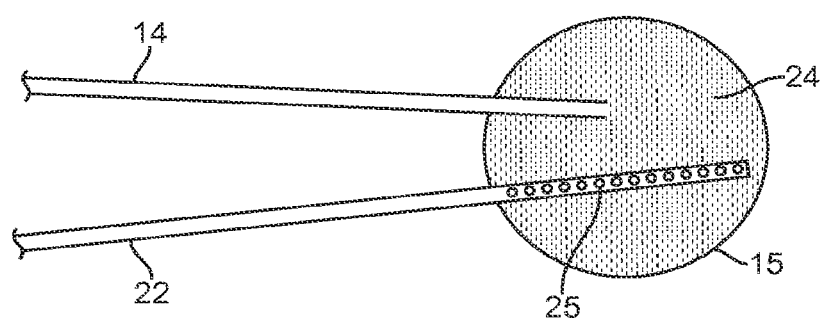
FIG. 7 depicts a close up schematic cross-section of the expandable member from FIG. 6.

FIG. 7 depicts a detailed embodiment of the expandable member 15 from FIG. 6 after the solution containing the initiator has been returned via tube 22. The resulting solution 24 undergoes polymerization. In order to ensure thorough mixing of returning solution containing initiator with delivered solution 26 in the expandable member, the distal portion of tube 22 is shown as extending essentially to the distal end of the expandable member. The distal portion of tube 22 also is shown as having a plethora of ports 25 spaced annularly around the distal portion of tube 22. In this manner, solution returning via tube 22 can mix more thoroughly with delivered solution 26 to ensure a more homogeneous mixed solution, and resulting in a uniform hydrogel polymer having the desired properties.

As described above, the catalyst may be incorporated in a source solution or introduced later in the process, either before or after introduction of the initiator. FIG. 8 depicts a portion of one embodiment of an apparatus 80 used to practice the present invention. In this embodiment two filter units 20A and 27 are connected in series. Filter unit 20A contains initiator 17A (or 17B) and filter unit 27 contains catalyst 29. Flowable aqueous solution comprising both polymer precursors flows into filter unit 20A, whereby the initiator dissolves therein, and then flows into filter unit 27 whereby the catalyst 29 dissolves therein, before being delivered to the expandable member 15. In a variation on this embodiment the two filter units are transposed so that the catalyst is introduced into the flowable aqueous solution before the initiator. The filter unit for the catalyst may be the same type as the filter unit for the initiator.

The following Examples are illustrative only and are not intended to limit the scope of other embodiments described in any way.

Example 1

A first source solution is prepared by mixing approximately equal weights of 0.01M pH 7.0 phosphate buffer and ethoxylated (20) trimethylolpropane triacrylate (PEG-T) (Sartomer Co., Exton, Pa.). A second source solution is prepared containing 4% (w/w) polyethylene glycol diacrylate 35,000 Da (PEG-D) (JenKem Technology, Allen, Tex.) in 0.01M pH 7.0 phosphate buffer. 22-23 ml of each of these source solutions was transferred to individual parallel chambers of a capped dual barrel syringe. 38 mg of ammonium persulfate powder (APS) was placed on the inlet side of a 33 mm Millex GP 0.22 μm filter disk and the disk was tapped to better distribute the powder. 55 mg of triethanolamine liquid (TEA) was placed on the inlet side of a second 33 mm Millex GP 0.22 μm disk. A multiple element static mixer was attached to the end of the dual barrel syringe. The dual barrel syringe was placed into a dispensing apparatus capable of dispensing equal volumes of the two solutions through the mixer. The filter containing the APS was attached to the mixer and the filter containing the TEA was attached in series to the outlet of the APS filter. Approximately 15 ml of each source solution (30 ml total) was dispensed, over 10-20 seconds, through the mixer and both filters sequentially into 3 glass vials placed in a 37° Celsius water bath, approximately 10 ml in each vial. Polymerization was observed in the first vial after seven minutes, resulting in a white solid hydrogel.

Example 2

Equal volumes (approximately 25 ml each) of the first and second source solutions from Example 1 were mixed to form a single source solution. Because only a capped dual barrel syringe was available, the resulting single source solution was transferred to both parallel chambers of the syringe, approximately 22-23 ml each, and a mixing tube was connected to the syringe, not for mixing purposes, but to provide an appropriate connector. A 33 mm Millex GP 0.22 μm filter disk containing 27 mg of TEA liquid was attached to the end of the mixing tube and a second 33 mm Millex GP 0.22 μm filter disk containing 32 mg of APS powder was attached in series to the outlet of the first filter. The dual barrel syringe was placed into a dispensing apparatus capable of dispensing equal volumes of the two solutions. Approximately 15 ml from each barrel (30 ml total) was dispensed, over 10-20 seconds, through the filters sequentially into 3 glass vials placed in a 37° Celsius water bath, approximately 10 ml in each vial. Polymerization was observed in the first vial after nine minutes, resulting in a white solid hydrogel.

Example 3

Example 1 is repeated, except that the filters are reversed so that the filter with the TEA is attached to the end of the mixer and the filter with the APS is attached in series to the outlet of the first filter. Polymerization is observed, resulting in a white solid hydrogel.

Example 4

Example 2 is repeated, except that the filters are reversed so that the filter with the APS is attached to the end of the mixing tube and the filter with the TEA is attached in series to the outlet of the first filter. Polymerization is observed, resulting in a white solid hydrogel.

Example 5

Example 1 is repeated, except that 92 mg of TEA is dissolved in the first source solution instead of being contained in a filter. Polymerization is observed, resulting in a white solid hydrogel.

Example 6

Example 2 is repeated, except that 45 mg of TEA is dissolved in the single source solution instead of being contained in a filter. Polymerization is observed, resulting in a white solid hydrogel.

Example 7

A first source solution was prepared by dissolving 4.8 g of PEG-D and 2.4 g of sodium diatrizoate in 112.8 g of 0.01M pH 5.0 phosphate buffer. A second source solution was prepared by dissolving 64.2 g of PEG-T and 1.128 g of triethanolamine in 64.8 g of 0.01M pH 5.0 phosphate buffer. 2.009 g ammonium persulfate was placed inside a polyurethane endobag. 60 ml each of the source solutions were mixed for 15 minutes to form a single source solution. That source solution was placed in a syringe and injected into the endobag at 21° Celsius without agitation to cure the hydrogel. Complete polymerization was observed after 22 minutes and 24 seconds, resulting in a solid white hydrogel.

The aforementioned embodiments according to the invention and apparatus used to practice such embodiments are illustrative only and are not intended to limit the scope of the claims hereinafter. Variations, modifications and combinations of the above embodiments will be apparent to the skilled practitioner and are included herein.

What is claimed is:

1. A system for treatment of an aneurysm in a patient, the system comprising:
    an expandable member that is inflatable and adapted for delivery into and expansion within the patient;
    a tube in fluid communication with a space inside the expandable member;
    a flowable aqueous solution comprising at least one polymer precursor; and
    a filter disposed in the tube upstream from the expandable member, the filter having upstream and downstream sides,
    wherein the filter is permeable to the flowable aqueous solution, and
    wherein the flowable aqueous solution forms a solid and substantially non-biodegradable material in the expandable member after passing through the filter.

2. The system of claim 1, wherein a free radical initiator in powder form is disposed on the upstream side of the filter such that as the flowable aqueous solution passes through the filter, the free radical initiator dissolves therein.

3. The system of claim 2, wherein the free radical initiator is a thermally activated low temperature free radical initiator.

4. The system of claim 2, wherein the flowable aqueous solution is a mixture of a first and a second source solution, wherein said first source solution comprises
    a first water soluble polymer precursor and the second source solution comprises a second water soluble polymer precursor.

5. The system of claim 4, further comprising an initiator catalyst, wherein either the first or second source solution comprises the initiator catalyst.

6. The system of claim 2, wherein the free radical initiator is sodium, potassium or ammonium persulfate.

7. The system of claim 2, further comprising an initiator catalyst, wherein the free radical initiator and the initiator catalyst are present in about a 1:1 molar ratio.

8. The system of claim 1, wherein the flowable aqueous solution comprises a first and a second water soluble polymer precursor, each water soluble polymer precursor comprising terminal functional groups.

9. The system of claim 8, wherein the first water soluble polymer precursor is linear and the second water soluble polymer precursor is branched.

10. The system of claim 9, wherein the molar ratio of the branched polymer precursor to the linear polymer precursor is between about 200:1 and about 1000:1.

11. The system of claim 9, wherein the molar ratio of the branched polymer precursor to a free radical initiator is between about 2:1 and about 15:1.

12. The system of claim 8, wherein the first water soluble polymer precursor is a linear polyethylene glycol terminally derivatized with two acrylate groups and having a molecular weight between about 20 and about 50 kiloDaltons, and the second water soluble polymer precursor is a branched oligomeric polyethylene glycol terminally derivatized with three acrylate groups and having a molecular weight between about 800 Daltons and about 1.2 kiloDalton.

13. The system of claim 1, wherein the expandable member is a double-walled balloon.

14. The system of claim 1, wherein the expandable member is configured to be implantable within the patient.

15. A method of forming an implant by increasing the volume of an expandable member for use in treatment of an aneurysm, the method comprising:
    a. introducing into a tube in communication with a space inside the expandable member, or directly into the expandable member, a flowable aqueous solution comprising a first and a second water soluble polymer precursor, each water soluble polymer precursor having terminal functional groups;
    b. introducing into the flowable aqueous solution from step (a) a thermally activated low temperature free radical initiator in powder form,
    c. allowing the free radical initiator to dissolve in the flowable aqueous solution, wherein the free radical initiator is disposed on a filter such that as the flowable aqueous solution passes through the filter, the free radical initiator dissolves therein;
    d. allowing functional groups on the water soluble polymer precursors to undergo covalent bonding to form a solid and substantially non-biodegradable material in the space inside the expandable member.

16. The method of claim 15, further comprising: introducing an initiator catalyst into the solution from step (c).

17. The method of claim 16, wherein, prior to step (a), there is introduced into a filling tube a source solution comprising the first and second water soluble polymer precursors and the initiator catalyst.

18. The method of claim 16, wherein either a first or second source solution comprises the initiator catalyst.

19. The method of claim 16, wherein the initiator catalyst is introduced before introduction of the initiator or the initiator catalyst is introduced after introduction of the initiator.

20. The method of claim 15, wherein the flowable aqueous solution is formed by the mixture of a first and a second source solution, wherein said first source solution comprises the first water soluble polymer precursor and the second source solution comprises the second water soluble polymer precursor.

21. A system for treatment of an aneurysm in a patient, the system comprising:
    an expandable member that is inflatable and adapted for delivery into and expansion within the patient;
    a tube in fluid communication with a space inside the expandable member; and
    a filter disposed in the tube upstream from the expandable member, the filter having upstream and downstream sides,
    wherein a free radical initiator in powder form is disposed on the upstream side of the filter such that as a flowable aqueous solution passes through the filter, the free radical initiator dissolves therein.

* * * * *